United States Patent
Zhang et al.

(10) Patent No.: US 7,457,709 B2
(45) Date of Patent: Nov. 25, 2008

(54) SYSTEMS AND METHODS FOR PARTICLE COUNTING

(75) Inventors: Shuliang Zhang, Miami, FL (US); Min Zheng, Pembroke Pines, FL (US); Dongqing Lin, Fargo, ND (US); Ziling Huo, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/312,722

(22) Filed: Dec. 20, 2005

(65) Prior Publication Data

US 2007/0143033 A1 Jun. 21, 2007

(51) Int. Cl.
G06F 19/00 (2006.01)
(52) U.S. Cl. .................. 702/26; 702/180; 73/61.71; 377/11; 377/12; 377/19
(58) Field of Classification Search ............. 702/21–26, 702/29–32, 77, 179–181, 199; 73/53.01, 73/61.71; 377/10–12, 19
See application file for complete search history.

(56) References Cited

U.S. PATENT DOCUMENTS

| 3,530,381 | A | * | 9/1970 | Klein et al. ............... 324/71.1 |
| 5,633,945 | A | | 5/1997 | Kamentsky |
| 6,744,245 | B2 | * | 6/2004 | Taylor et al. .............. 324/71.4 |
| 2003/0020447 | A1 | | 1/2003 | Taylor et al. |
| 2003/0078703 | A1 | * | 4/2003 | Potts et al. ................... 701/1 |
| 2005/0211606 | A1 | | 9/2005 | Harshbarger et al. |

OTHER PUBLICATIONS

Wynn et al., "Coincidence correction for electrical-zone (Coulter Counter) particle size analysers", Powder Technology 93, pp. 163-175 (1997).*
Wynn, E.J.W., et al., "Coincidence correction for electrical-zone (Coulter-counter) particle size analysers", Powder Technology 93, pp. 163-175 (1997).
Gonzalez, R.C., et al., "Digital Image Processing", Addison-Wesley Pub., pp. 580-586 (1993).
Coulter LH 700 Series System reference manual, 114 pages (Oct. 2003).
Coulter®$A^C$ T Series Analyzer Reference Manual, Coulter Corporation, 100 pages (1997).
International Search Report and Written Opinion for Int'l Appl. No. PCT/US/ 06/61029, 7 pages, dated Feb. 13, 2008.
Ferman et al, "Robust Color Histogram Descriptors for Video Segment Retrieval and Identification," IEEE Transactions on Image Processing, vol. 11, No. 5, May 2002, pp. 497-508, (abstract).
Yazici, B. "Statistical Pattern Analysis of Partial Discharge Measurements for Quality Assessment of Insulation Systems in High-Voltage Electrical Machinery," IEEE Transactions on Industry Applications, vol. 40, No. 6, Dec. 2004, (abstract).

* cited by examiner

*Primary Examiner*—Manuel L Barbee
(74) *Attorney, Agent, or Firm*—Sterne, Kessler, Goldstein & Fox P.L.L.C.

(57) ABSTRACT

Systems and methods consistent with embodiments of the present invention provide a method for the measurement and analysis of particle counts in flow cytometry and hematology instruments. In some methods for the measurement and analysis of particle counts, a corrected histogram of particle distributions is calculated and used to obtain an accurate count of particles and an accurate measurement of other particle parameters.

8 Claims, 12 Drawing Sheets

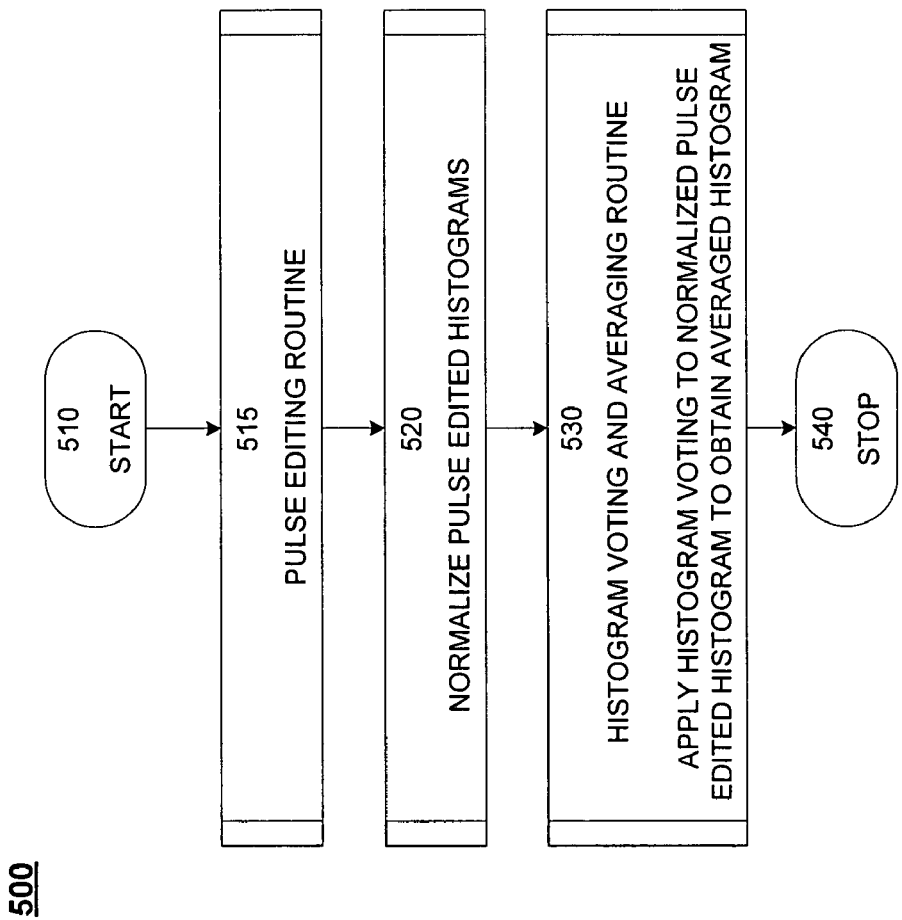

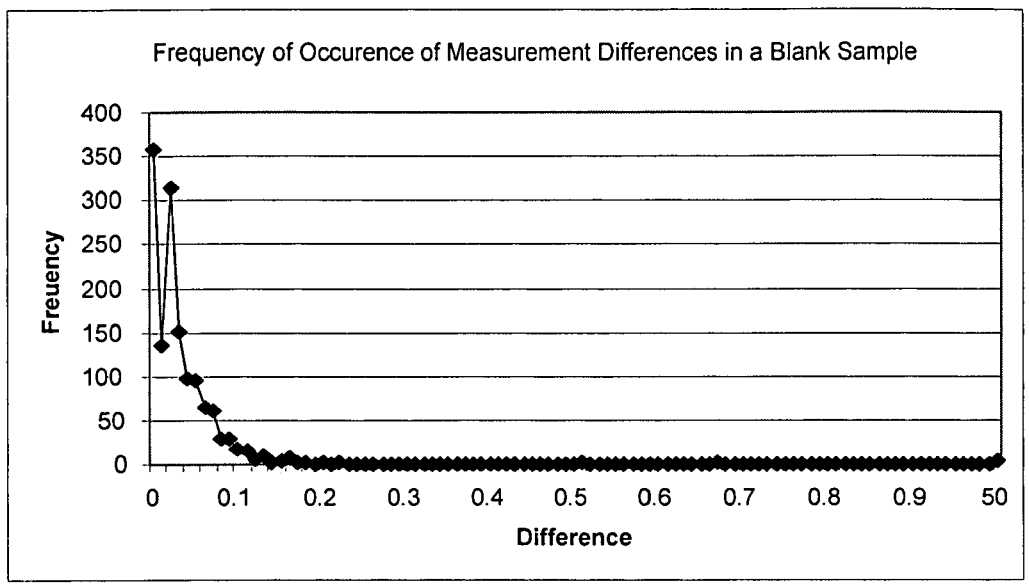
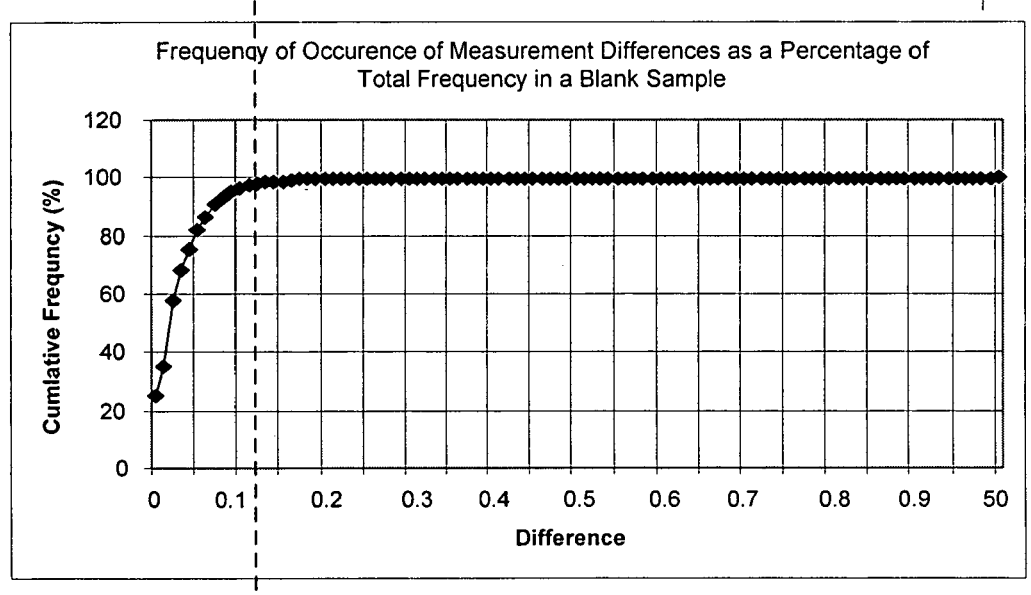
FIG. 6B

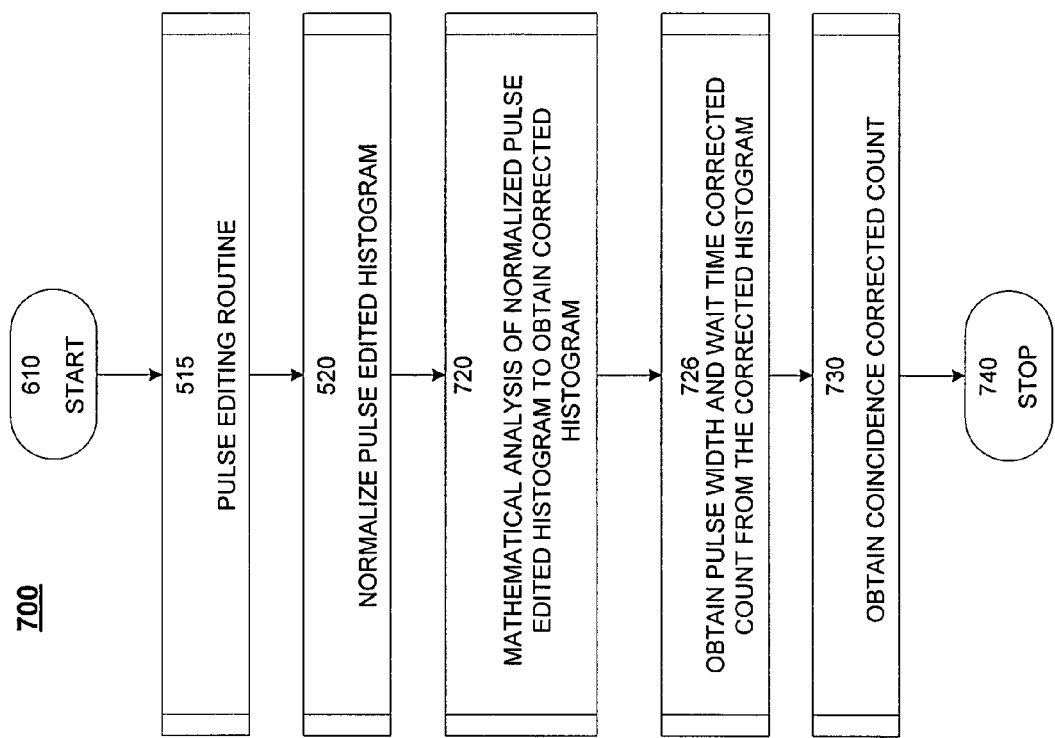

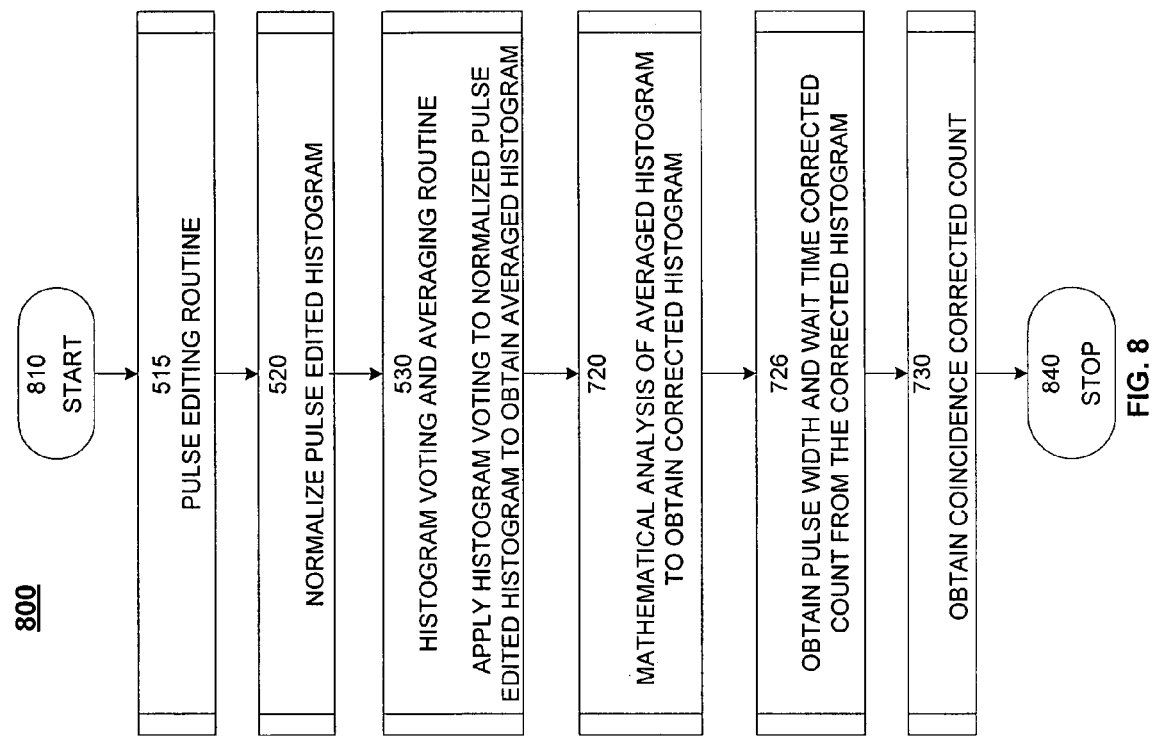

SYSTEMS AND METHODS FOR PARTICLE COUNTING

FIELD OF THE INVENTION

This present invention relates to the field of flow cytometry and, in particular, to systems and methods for particle counting and analysis in flow cytometers.

DESCRIPTION OF RELATED ART

Beckman Coulter, COULTER®, Coulter Counter™, Epics®, Cytomics, FC 500, LH750, and LH755 are trademarks and/or registered trademarks of Beckman Coulter, Inc.

Flow cytometry is extensively used in biological, chemical, and bio-chemical applications. Flow cytometers may be used for particle counting and analysis, including cell counting and sorting, cell surface and intracellular antigen measurements, and for DNA analysis. Flow cytometers may exploit differences in one or more particle characteristics to count and classify particles. For example, Red Blood Cells ("RBCs") typically range from 5 to 8 microns in diameter, whereas White Blood Cells ("WBCs") range from 10 to 12 microns, while platelets range from 2 to 4 microns in diameter. Flow cytometers may exploit the size difference between RBCs, WBCs, and platelets to count and classify the cells in a tissue sample.

Although cell counting has typically revolved around the measurement of the number of RBCs, WBCs, and Platelets in a blood sample, modern flow cytometers are capable of a greater variety of measurements including the measurement of liver, kidney, and skin-cell concentrations. Cell counting and sorting is important because an automated count of blood cells can be used to obtain a picture of a persons overall heath. For example, in patients infected with the Human Immunodeficiency Virus ("HIV"), the ratio of CD4 type cells to CD8 type cells is used to determine when a patient has transitioned from an HIV infection to full blown Acquired Immune Deficiency Syndrome ("AIDS").

In flow cytometers that employ the electrical sensing zone method such as Coulter Counters™, for example, an electrical signal such as an electrical pulse may be generated when a particle, such as a blood cell, traverses a sensing zone of the flow cytometry instrument. The height of the pulse, for example, may be proportional to the size of the particle traversing the sensing zone. Accuracy, however, is affected by coincidence, which occurs when multiple particles enter the sensing zone almost simultaneously; by misshapen pulses caused by coincidence, or by particles traversing the sensing zone with unusual trajectories; and by malfunctions within the instrument—such as a sensor malfunction. Coincidence, misshapen pulses, and instrument malfunctions may operate individually, or in conjunction to limit the operating range, accuracy, and reliability of particle counters, such as flow cytometers.

In hematological measurements, an inaccurate or questionable count may require the measurement and analysis to be repeated on the measuring instrument, or a manual cell count to be conducted by a trained laboratory technician. Recounts are time-consuming and expensive. Moreover, the availability of additional blood samples for any retest may present additional problems. In short, confirming the accuracy of automated cell counts is a time-consuming and costly activity for most hematology laboratories, and any delay in communicating accurate results may have a detrimental impact on patient management decisions. Thus, there is a need for techniques to further reduce the measurement distortions and inaccuracies that occur in particle counting instruments, and to increase the operating range and reliability of particle counting instruments.

SUMMARY OF THE INVENTION

In accordance with the invention, systems and methods to obtain an accurate measurement of particle parameters is disclosed. In some embodiments the method comprises generating a normalized histogram by selecting captured electrical signals wherein a captured electrical signal is associated with one of one or more sensors in a flow cytometer instrument. In some embodiments, a corrected histogram is obtained based on a mathematical analysis of the normalized histogram and a probability that at any instant there is at least one particle in the sensing zone; and a corrected particle count is calculated based on the corrected histogram.

In some embodiments, generating the normalized histogram may further comprise comparing parameters of each captured electrical signal with corresponding reference parameter ranges; choosing captured electrical signals whose parameters fall within corresponding reference parameter ranges; generating at least one edited histogram for each sensor using the chosen electrical signals associated with the sensor; rejecting an edited histogram associated with a sensor, if the edited histogram differs from all distinct edited histograms associated with other sensors; averaging all non-rejected edited histograms; and normalizing the averaged histogram. In some embodiments, a similarity score may be computed and used to determine if a histogram is different from other histograms.

In some embodiments, generating the normalized histogram may also comprise comparing parameters of each captured electrical signal with corresponding reference parameter ranges; choosing captured electrical signals whose parameters fall within corresponding reference parameter ranges; generating at least one edited histogram for a sensor using the chosen electrical signals associated with the sensor; and normalizing the edited histogram.

In some embodiments, obtaining a corrected histogram may further comprise performing a Fourier transform on the normalized histogram generated from the selected electrical signals; calculating a Fourier transform of the corrected histogram based on the fast Fourier transform of the normalized histogram and a probability that at any instant there is at least one particle in the sensing zone; and obtaining the corrected histogram by computing the inverse of the Fourier transform of the corrected histogram. In some embodiments, fast Fourier methods may be used in the computations of the Fourier transform and the inverse Fourier transform.

In some embodiments, a wait time corrected count and a coincidence corrected count may be calculated based on some function of the mean and/or mode of the signal height in the corrected histogram. In some embodiments, the method may be applied to solutions with high concentrations of particle-counts.

Some embodiments of the present invention also pertain to apparatus, systems, and stored instructions for obtaining an accurate measurement of particle parameters. Additional objects and advantages of the invention will be set forth in part in the description, which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate some embodiments of the invention and together with the description, serve to explain the principles of the invention.

FIG. 5 shows an exemplary flowchart depicting steps in an algorithm for measurement and analysis of particle parameters according to some embodiments of the present invention.

FIG. 6B shows exemplary histograms plotting the frequency of occurrence of various measurement differences and the cumulative frequency of occurrence of a measured difference as a percentage of the total frequency

FIG. 7 shows an exemplary flowchart depicting steps in an algorithm for measurement and analysis of particle parameters according to some embodiments of the present invention.

FIG. 8 shows an exemplary flowchart depicting steps in an algorithm for measurement and analysis of particle parameters according to some embodiments of the present invention.

DESCRIPTION OF THE EMBODIMENTS

Reference will now be made in detail to some embodiments of the present invention, examples of which are illustrated in the accompanying drawings. Wherever possible, the same reference numbers will be used throughout the drawings to refer to the same or like elements.

In accordance with the invention, systems and methods to obtain an accurate measurement of particle parameters are disclosed. In some methods, the effects of particle coincidence, misshapen signals or pulses, and instrument malfunctions may be reduced and/or minimized in order to obtain an accurate measurement and an analysis of particle parameters. Methods to correct for the effects of coincidence have been proposed. See, for example, E. J. W. Wynn and M. J. Hounslow, "Coincidence correction for electrical-zone (Coulter-counter) particle size analysers," Powder Technology 93, pp. 163-175, Elsevier Science S. A., 1997 ("Wynn"), which is herein incorporated by reference in its entirety. In Wynn, the numerical Fourier transform is used for coincidence correction. See also, U.S. Pat. No. 6,744,245 B2 to R. L. Taylor and M. Zheng, entitled "Particle count correction method and apparatus," which is herein incorporated by reference in its entirety.

Figure 1:
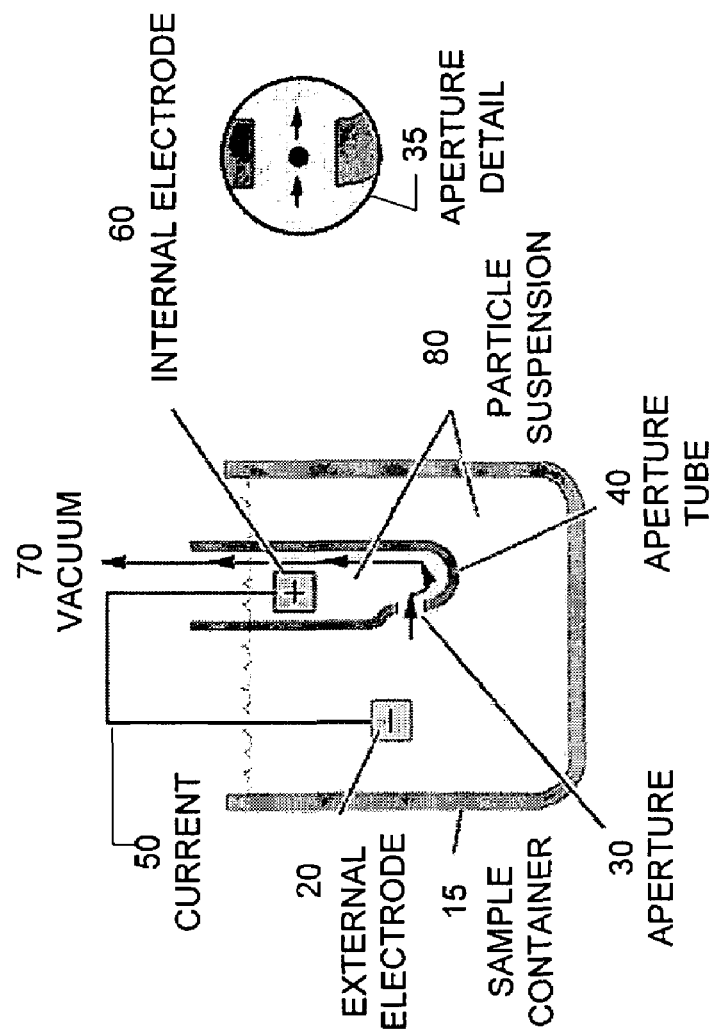
FIG. 1 shows an exemplary apparatus to illustrate operating principles of an electrical sensing zone type instrument for the measurement of particle counts according to some embodiments of the present invention.

FIG. 1 shows an exemplary apparatus to illustrate the operating principles of an electrical sensing zone type instrument for the measurement of particle counts. As shown in FIG. 1, sample container 15 includes aperture tube 40 with an aperture 30. Current 50 flows between internal electrode 60 disposed within aperture tube 40 and external electrode 20 disposed outside the aperture tube. Sample container 15 may hold particles suspended in fluids such as particle suspension 80. Vacuum 70 draws particle suspension 80 through aperture 30.

Particles may comprise blood cells, other biological cell types, silica particles, clay particles, pellets, latex particles, or any other type of particle capable of being measured by flow cytometry type instruments. When particle suspension 80 passes through aperture 30 simultaneously with electric current 50, individual particles passing through aperture 30 introduce an impedance change in aperture 30 proportional to the size of the particle. Aperture detail 35 shows a particle passing through aperture 30. The impedance change begins to occur when the particle passes within a sensing zone and is detectable as an electrical signal, for example, as an electrical pulse. The height of the electrical pulse is proportional to the size of the particle.

Particle counters such as Coulter Counters™ can also sort the particle counts into different "bins" based on the number of particles of a given size or size range. A bin corresponds to a range of the particle size data. For each bin, the number of particles from the data set that fall into the bin are counted. In addition, some flow cytometry instruments may be capable of generating a histogram of the frequencies of occurrence of particles of different sizes.

It should be noted that the above description relating to electrical sensing zone type cytometers is exemplary, and only for the purposes of illustrating the principles of operation of flow cytometers. In general, flow cytometers may use a variety of methods for detection of particles including methods based on the use of fluorescence, light scattering, pyrometry, and lasers. Techniques and methods of the present invention apply to all particles that may be sensed by a flow cytometer. The described techniques and methods may be adapted for use on the various types of flow cytometers in a manner consistent with principles of the present invention.

Figure 2:
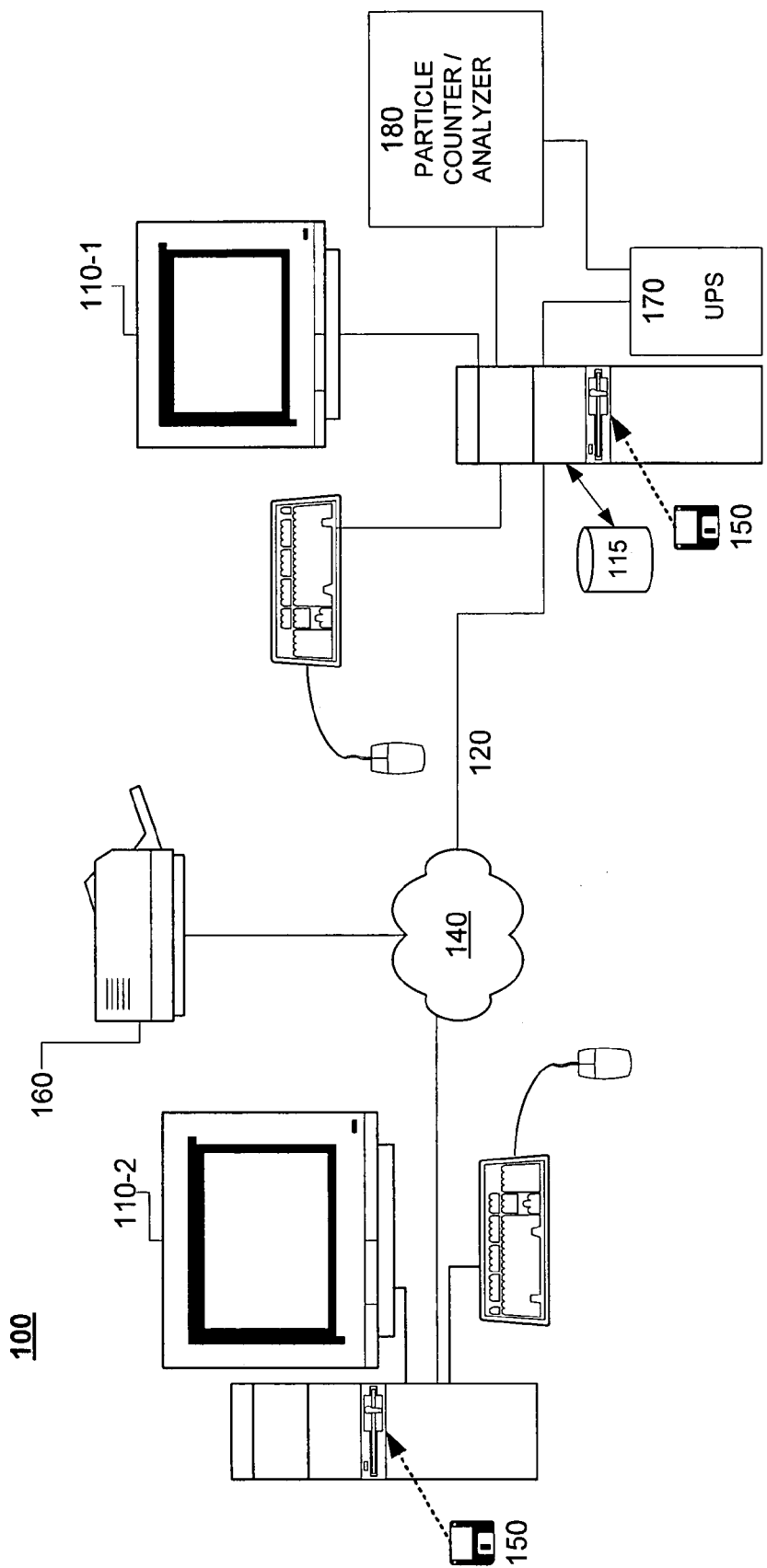
FIG. 2 shows an exemplary system for the measurement and analysis of particle parameters according to some embodiments of the present invention.

FIG. 2 shows an exemplary system for the measurement and analysis of particle parameters according to some embodiments of the present invention. A computer software application consistent with the present invention may be deployed on system 100, as shown in FIG. 2, that are coupled through communication links that allow information to be exchanged using conventional communication protocols and/or data port interfaces.

As shown in FIG. 2, exemplary system 100 includes computing devices 110-1 and 110-2, printer 160 and particle counter/analyzer 180. Further, computing devices 110-1 and 110-2 may communicate over a connection 120, which may pass through network 140. Computing device 110 may be a computer workstation, desktop computer, laptop computer, server, handheld computer, or any other computing device capable of being used in a networked environment.

Computing device 110 may be capable of executing software (not shown) that allows the measurement and analysis of particle parameters according to some embodiments of the present invention. Exemplary computing device 110 also contains removable media drive 150. In some embodiments, removable media drive 150 may include, for example, 3.5 inch floppy drives, CD-ROM drives, DVD ROM drives, CD±RW or DVD±RW drives, USB flash drives, and/or any other removable media drives. In some embodiments, portions of the software application may reside on removable media and be read and executed by computing device 110 using removable media drive 150.

Connection 120 couples computing devices 110-1 and 110-2, particle counter/analyzer 180, and printer 160, and may be implemented as a wired or wireless connection using conventional communication protocols and/or data port interfaces. In general, connection 120 can be any communication channel that allows transmission of data between the devices. In some embodiments, computing devices 110-1 and 110-2, particle counter/analyzer 180, and printer 160 may be provided with conventional data ports such as Ethernet, USB, SCSI, and/or Firewire ports for transmission of data through the appropriate connection 120. The communication links could be wireless links or wired links or any combination that allows communication between computing devices 110-1 and 110-2, particle counter/analyzer 180, and printer 160. Network 140 could include a Local Area Network (LAN), a Wide Area Network (WAN), or the Internet. In some embodiments, information sent over network 140 may be encrypted to ensure the security of the data being transmitted. Encryption protocols are generally well-known and/or commercially available.

Printer 160 is coupled to network 140 through connection 120. In some embodiments, printer 160 may be connected directly to computing device 110-1, computing device 110-2, and/or particle counter/analyzer 180. System 100 may also include other printers 160 (not shown) according to some embodiments of the invention. In some embodiments, printer 160 may be a network printer and provide communication ports, including multiple ports for receiving data. In some embodiments, printer 160 may print results or other types of reports generated by computing device 110-1, computing device 110-2, and/or particle counter/analyzer 180.

In some embodiments, a computer software application for the measurement and analysis of particle parameters may be deployed on any of the exemplary computers 110, or particle counter/analyzer 180, as shown in FIG. 2. For example, computing devices 110-1 and 110-2, and/or particle counter/analyzer 180 may execute software resident on storage media, or in memory coupled to the respective devices. In some embodiments, the software application may be distributed across computing devices 110-1, 110-2, and particle counter/analyzer 180 so that portions of the software application may be executed by one or more of the components. It should be noted that system 100 is exemplary only and that a computer software application for the measurement and analysis of particle parameters may be executed entirely by a computing device, such as computing device 110-1 coupled to particle counter/analyzer 180.

In some embodiments, particle counter/analyzer 180 may be flow cytometry instrument. In some embodiments, particle counter/analyzer 180 may be a Coulter Counter™. Flow cytometers may include Epics® flow cytometer or Cytomics FC 500 flow cytometer, both of which are available from Beckman Coulter (Miami, Fla.). In some embodiments, particle counter/analyzer 180 may also be a hematology analyzer such as a COULTER® LH755, COULTER® LH750, COULTER® Gen•S™, and COULTER® HmX, all of which are available from Beckman Coulter (Miami, Fla.).

In some embodiments, particle counter/analyzer 180 may have a processor, or an application specific integrated circuit ("ASIC") to process pulse data generated when particles traverse a sensing zone in the particle counter/analyzer 180. In some embodiments, particle counter/analyzer 180 may have memory including PROM, ROM, RAM, flash memory, or NVRAM, which may hold instructions and/or data for a processor or ASIC to execute portions of an algorithm for the measurement and analysis of particle parameters according to some embodiments of the present invention. In some embodiments, a computer software application for the measurement and analysis of particle parameters may be executed entirely by particle counter/analyzer 180. In some embodiments, particle counter/analyzer 180 may operate in a stand-alone environment without computing devices 110 and perform steps in a method for the measurement and analysis of particle parameters. In some embodiments, hardware, software, or firmware on an existing particle counter/analyzer 180 may be upgraded and/or replaced to execute algorithms for the measurement and analysis of particle parameters.

In some embodiments, particle counter/analyzer 180 may transmit pulse data to coupled computing device 110-1, which may execute an algorithm for the measurement and analysis of particle parameters according to some embodiments of the present invention. In some embodiments, data recorded by particle counter/analyzer 180, and any intermediate and final results may be stored in database 115 coupled to computing device 110-1. In general, one or more databases such as exemplary database 115 may be coupled to various computing devices 110 and/or particle counter/analyzer 180 according to some embodiments of the present invention. In some embodiments, a software program for the measurement and analysis of particle parameters may be downloaded by computing device 110-1 from computing device 110-2 over network 140.

In some embodiments, one or more components of system 100 may be coupled to uninterruptible power supply ("UPS") 170, to minimize the effect of power line fluctuations and to provide back-up power in case of a power failure.

Figure 3:
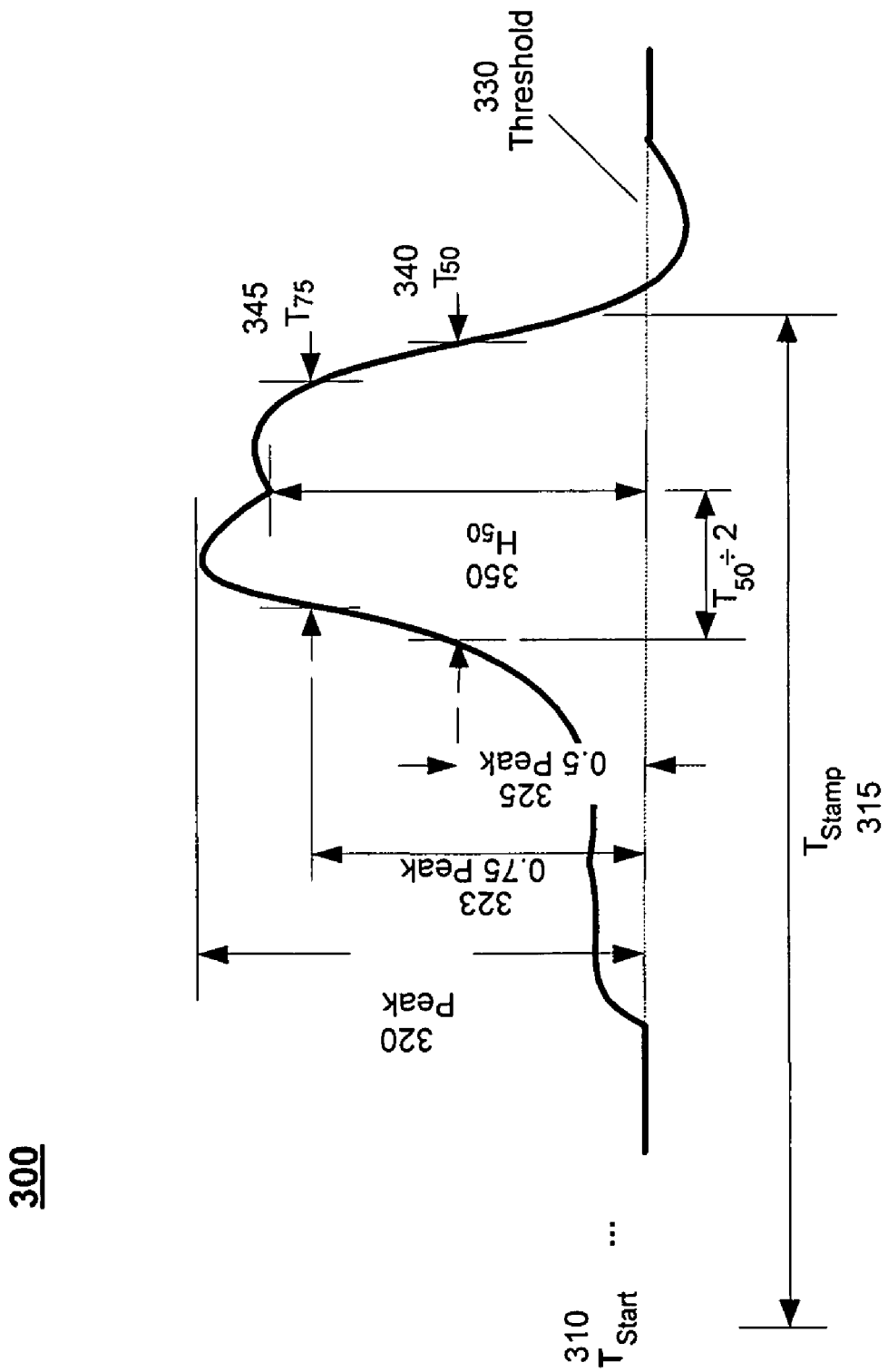
FIG. 3 shows an exemplary pulse illustrating various parameters used in the measurement and analysis of particle parameters according to some embodiments of the present invention.

FIG. 3 shows an exemplary (misshapen) pulse illustrating various parameters used in the measurement and analysis of particle parameters according to some embodiments of the present invention. In some embodiments, these parameters may be used to set up criteria to identify aberrant pulses.

The accuracy of a particle count may be adversely affected if the electrical pulse is misshapen. Misshapen pulses may be caused by particles traversing the sensing zone with unusual trajectories, or by coincident particles. Misshapen pulses are difficult to categorize and create uncertainties with regard to particle counts. A misshapen pulse may be incorrectly classified as noise, as a particle of a different size, or as multiple particles depending on the size and/or shape of the pulse. To minimize measurement inaccuracies caused by misshapen pulses, some particle counters employ pulse-editing circuitry or software to remove aberrant pulses. However, a simple removal of all aberrant pulses may result in a lower measurement of total particle volume. In some methods, pulse-editing techniques based on one or more functions of parameters shown in FIG. 3 may be combined with other methods disclosed in this application in order to accurately measure and analyze particle parameters.

As shown in FIG. 3, Pulse 300 is an M-shaped pulse that may be generated by particle counter/analyzer 180 during measurement. Parameter $T_{Start}$ 310 denotes the time at which measurement is started. Parameter $T_{Stamp}$ 315 denotes the time at which the pulse is recorded. Parameter Peak 320 is the maximum amplitude above predefined threshold 330, while 0.75 Peak 323 and 0.5 Peak 325 represent 75% and 50% of Peak parameter 320, respectively. In some embodiments, threshold 330 may be set above the noise level of the environment in which testing is conducted. Parameter Peak 320 is an indication of the size of the particle that caused the pulse. Parameter T50 340 is the time interval (horizontal axis) between the two points where the amplitudes are half the peak amplitude on the rising and descending side of the peak, respectively. Parameter T75 345 is the time interval (horizontal axis) between the two points where the amplitudes are 0.75 of the peak amplitude. Parameter H50 350 is the amplitude at the midpoint of the time interval between the two points where the amplitudes are half the peak amplitude on the rising and descending side of the peak, respectively.

Figure 4:
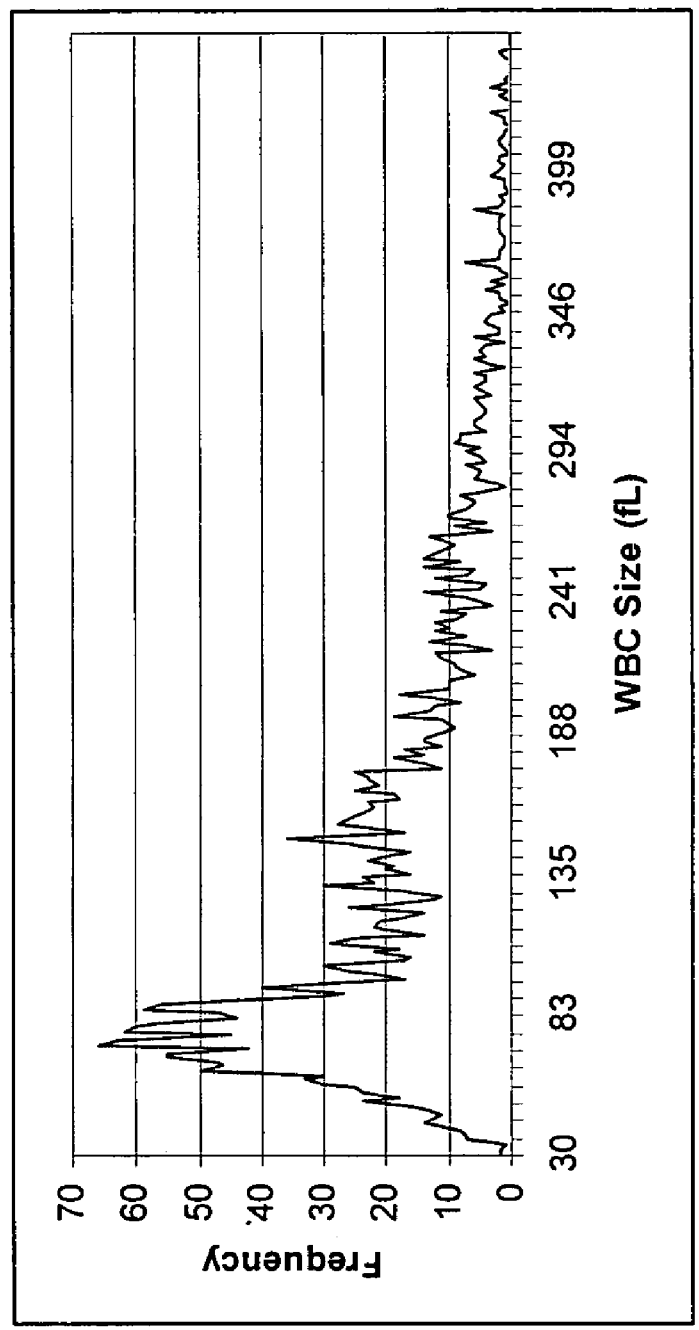
FIG. 4 shows an exemplary histogram illustrating the distribution of particles of different sizes.

FIG. 4 shows an exemplary histogram illustrating the distribution of particles of different sizes. In FIG. 4, particle volume in femto liters ("fL") is depicted on the X-axis. Note that 1 fL=$10^{-15}$ liters. In FIG. 4, particles range in size from 30 fL to 450 fL. In some embodiments, the particles may be placed in various bins based on their sizes. In FIG. 4, each bin has a bin size of 1.65 fL. Therefore particles that differ in size by more than 1.65 fL fall into different bins. The y-axis represents the frequency of occurrence, or the count of particles in each bin. FIG. 4 shows a raw histogram of using the absolute counts of the particles.

In some embodiments, a histogram, such as the one shown in FIG. 4, may be subjected to a normalization procedure. The normalized histogram uses the relative frequency distribution of the particles. The value of the relative frequency for a bin is given by the absolute count of particles in the bin divided by the total count. Accordingly, the cumulative frequency of particles in the normalized histogram is one.

In some embodiments, particle counters may use more than one particle sensor to enhance the reliability of measurements. Flow cytometry instruments may report inaccurate counts on account of instrument malfunction. For example, a particle sensor within the instrument may malfunction and report an inaccurate count. To alleviate this problem and enhance the reliability of measurements generated by an instrument, three or more sensors may be used instead of one. When three sensors are used in an instrument, if the total count of particles by one of the sensors differs from the other two by more than some predetermined number then the particle count by the aberrant sensor can be voted out. If all three sensors disagree by more than the specified number then the entire count can be rejected and a new run ordered. However, the use of the total particle count to detect sensor malfunctions may be limited by instrument and background noise levels and by other factors especially at low particle concentration levels. In addition, the total particle count, while useful, is only a very approximate discriminant of count accuracy and consequently may not accurately detect or report sensor malfunction.

Particulate concentration levels in samples may vary depending on the type of sample and instrument characteristics. For example, with WBCs, high concentration samples may be those with a WBC count greater than $10^5$ particles per micro liter. A normal WBC count is generally between $4 \times 10^3$ to $11 \times 10^3$ counts per micro liter. Both high and low particulate concentrations affect measurement. At low particulate concentrations noise and other factors may affect measurements, while at high particulate concentrations coincidence may affect measurements.

FIG. 5 shows a flowchart 500 illustrating steps in an exemplary algorithm for enhancing the reliability of measurements made by a multi-sensor particle counter. In some embodiments, the particle counter may comprise of three sensors. The algorithm commences in step 510 and then proceeds to pulse editing routine 515. Pulses are expected to have symmetric Gaussian-like curves when all the particles travel through the center of the aperture. However, misshapen pulses may be caused by particles traversing the sensing zone with unusual trajectories, or by coincident particles. In some embodiments, pulse editing routine may identify and eliminate misshapen pulses in step 515.

In some embodiments, the pulse editing routine may use one or more of the parameters identified in FIG. 3 (and described above) individually, or in combination, to identify and eliminate aberrant pulses in step 515. In some embodiments, a pulse may be eliminated by pulse editing routine in step 515 if parameters T50 340 and T75 345 of the pulse do not fall within an expected range. In some embodiments, the expected ranges of parameters T50 340 and T75 345 of a pulse may be based on the configuration of particle counter/analyzer 180. In some embodiments, a pulse may be eliminated by pulse editing routine in step 515 if the ratio of parameters T75 345 to T50 340 does not fall within an expected range. In some embodiments, the ratio of parameters T75 345 to T50 340 may be estimated based on the configuration of particle counter/analyzer 180. In some embodiments, a pulse may be eliminated by the pulse editing routine in step 515 if the ratio of parameters Peak 320 to H50 350 does not fall within an expected range. In some embodiments, the ratio of parameters Peak 320 to H50 350 may be estimated based on the configuration of particle counter/analyzer 180.

In some embodiments, a ratio of parameters, or a function of one or more parameters may be used to establish criteria for the identification and elimination of misshapen pulses. For example, ranges (in microseconds) may be established for T50 340 and T75 345. Acceptable T50 340 to T75 345 ratios and Peak 320 to H50 350 ratios may also be established. The actual ranges chosen for T50 340 and T75 345 may be based on system configuration parameters such as aperture length, fluid flow rates, and/or expected particle size ranges. In some embodiments, statistical and/or empirical methods may be used to establish the ranges and ratios. In some embodiments, the ratios and ranges help to identify and select symmetric and near-symmetric pulses, and to identify and eliminate M-shaped pulses.

In step 520, the pulse edited histogram obtained at the completion of the pulse editing routine in step 515 may be normalized according to some embodiments of the present invention. In some embodiments, normalization may involve the computation or re-computation of the relative frequencies of occurrence for each of the individual bins in the histogram based on the total number of pulses remaining after step 515. In some embodiments, the number of pulses remaining in each bin (following the removal of aberrant pulses) may be divided by the total number of remaining pulses to obtain the relative frequencies of occurrence for each of the individual bins.

In some methods for obtaining an accurate measurement of particle parameters the effects of background noise levels on particle counts and any consequent effects on the voting procedure may be reduced. In addition, the voting step may be based on the entire individual normalized histograms to accurately measure and analyze particle parameters. In some embodiments, a voting step may be applied to the individual normalized histograms as part of histogram voting and averaging routine 530. In histogram voting and averaging routine 530, a histogram that is determined to be different from the other two histograms is voted out.

Figure 6A:
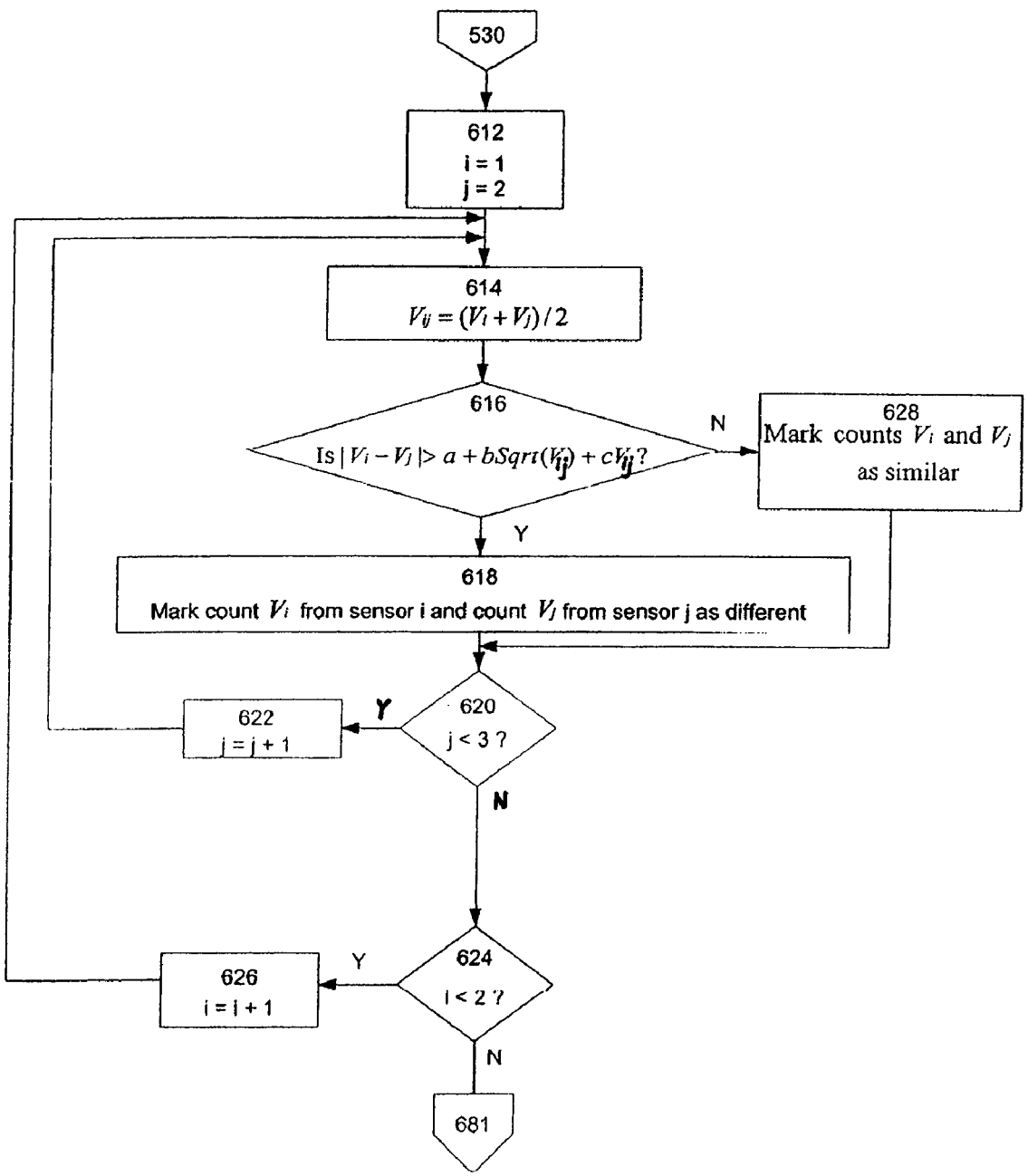
FIG. 6A shows an exemplary flowchart depicting steps in a method for determining when a particle count measured by a sensor is considered different from that measured by another sensor in a three-sensor particle counter.
Figure 6C:
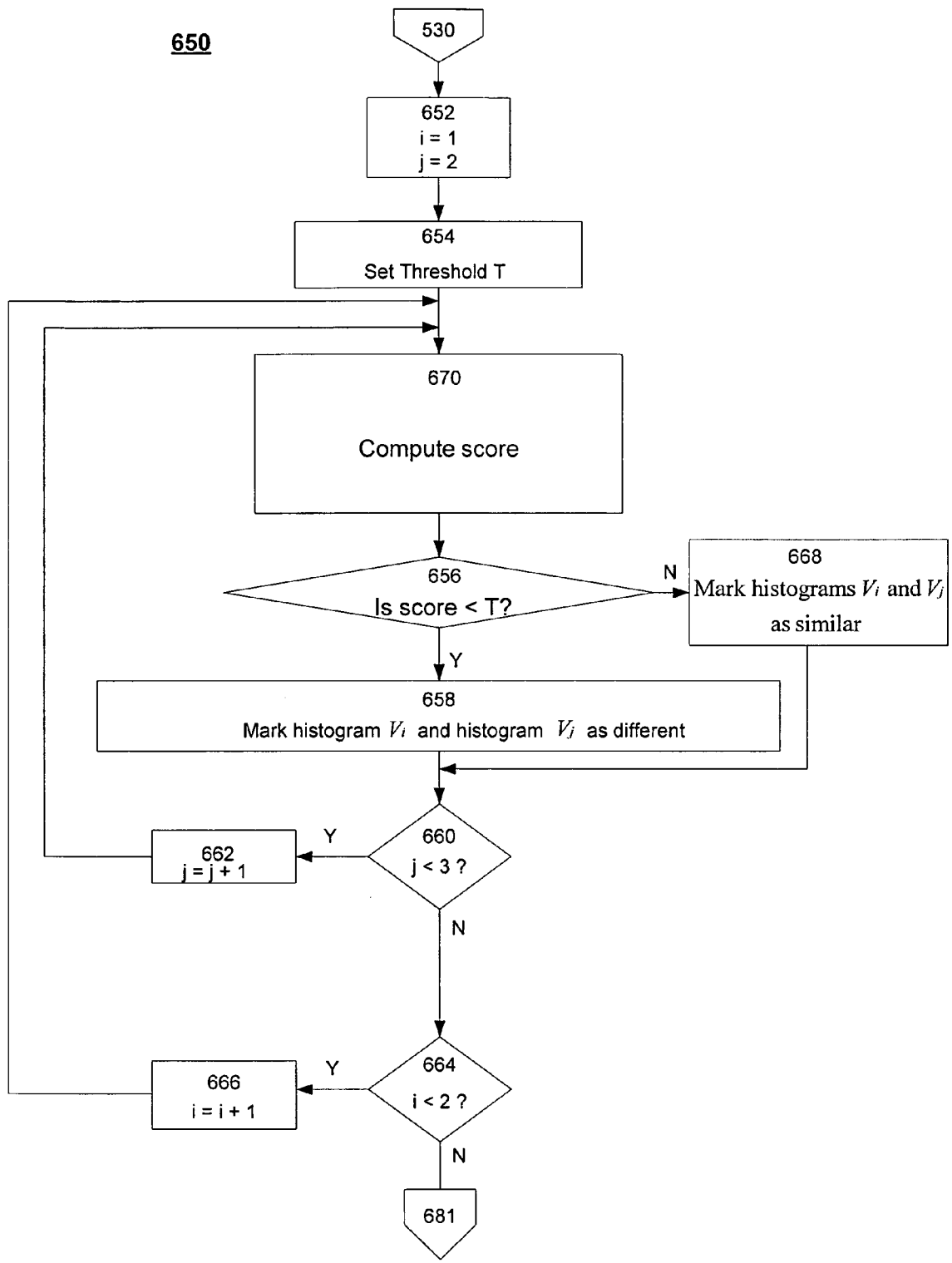
FIG. 6C shows an exemplary flowchart depicting steps in an alternate method for determining when a particle count measured by a sensor is considered different from that measured by another sensor in a three-sensor particle counter.
Figure 6D:
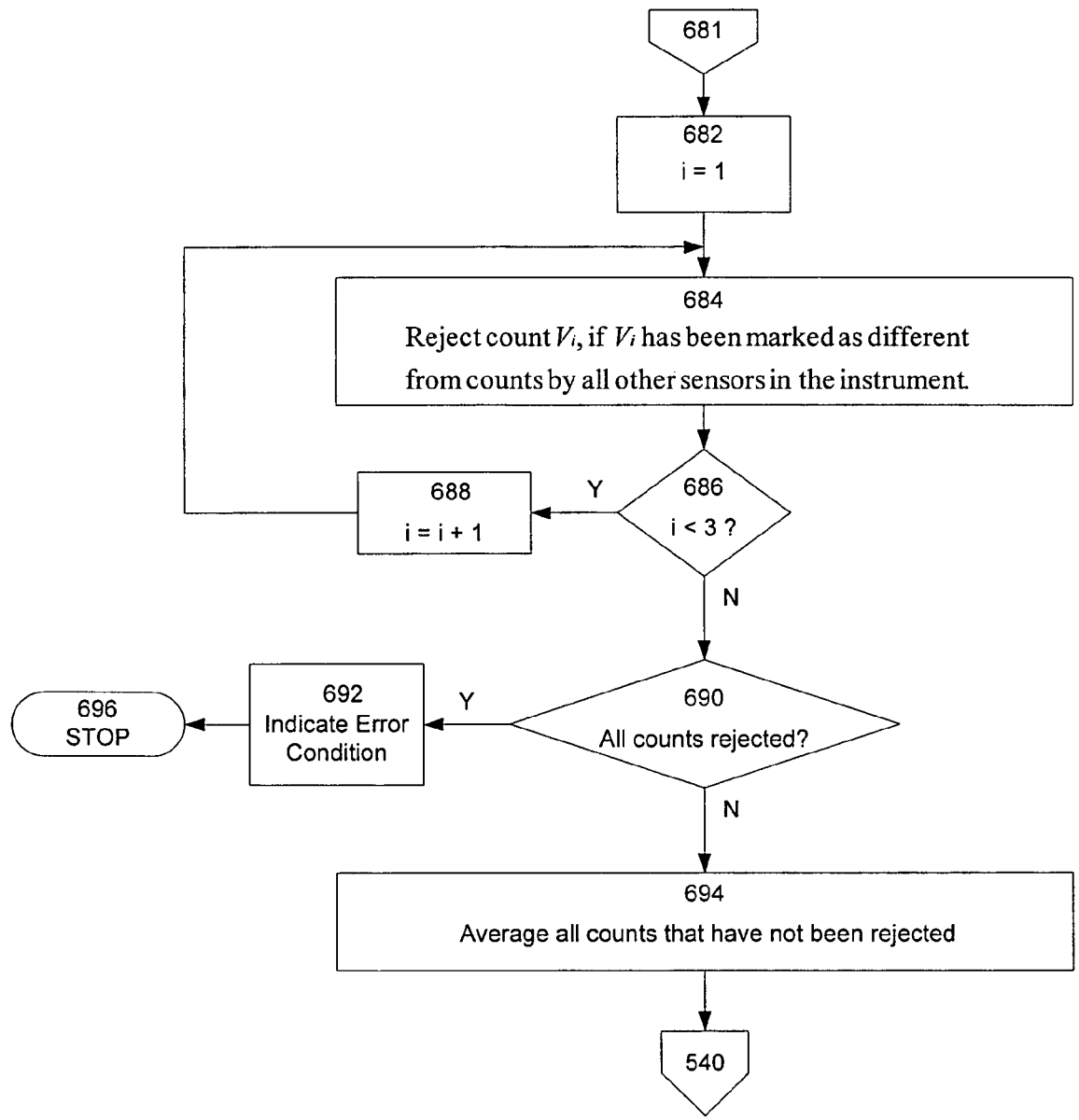
FIG. 6D shows an exemplary flowchart illustrating steps in an algorithm to determine when the particle count by a sensor should be rejected.

In some embodiments, one or more algorithms such as exemplary algorithms illustrated in FIGS. 6A, 6C, and 6D may be used to determine if a sensor has malfunctioned so that measurements made by that sensor may be voted out. In some embodiments, some or all of histogram voting and averaging routine 530 may be executed by one or more of the algorithms depicted in the exemplary flowcharts shown in FIGS. 6A, 6C, and 6D. In some embodiments, if all histograms are voted out, an operator may be alerted regarding a possible instrument malfunction. In some embodiments, if the measurement by a sensor is voted out an operator may be alerted to the possible malfunctioning of the sensor. In some embodiments, if a sensor is voted out the measurements made by the other sensors may be averaged. In some embodiments, histograms may be averaged by averaging particle counts for corresponding bins in the various histograms.

Note that the steps depicted in flowchart 500 are exemplary only and that the order of steps may be varied in a manner consistent with the invention. For example, the voting routine of step 530 may be applied to pulse edited data, prior to normalizing the histogram.

FIG. 6A shows an exemplary flowchart 600 depicting steps in a method for determining when a particle count measured by a sensor is different from that measured by another sensor in a three-sensor particle counter. In FIG. 6A, $V_i$ denotes the particle count measured by sensor i, and $V_{ij}$ denotes the average of counts $V_i$ and $V_j$ measured by sensors i and j, respectively. In flowchart 600, counts by two sensors i and j are considered different if $|V_i-V_j|>a+b \, \text{Sqrt}(V_{ij})+cV_{ij}$, where a, b, and c are instrument and/or measurement-environment related parameters as described below, and $\text{Sqrt}(V_{ij})$ denotes the square root of $V_{ij}$. In some embodiments, as shown in FIG. 6A, a determination of whether the particle counts of two sensors are markedly different may be made based on the total particle counts by the individual sensors and instrument and/or measurement-environment related parameters. In some embodiments, the described techniques and methods may allow for more accurate counts at low particulate concentration levels.

In FIG. 6A, the constant a may be related to the background noise level of the instrument. When a sample without a discernible particulate suspension is run through a particle counter, the instrument may report a non-zero particle count. For example, in a fluid suspension micro-bubbles generated in the fluid may be mistaken for particles and cause a non-zero particle count. The background noise level varies randomly and may impact the measurement made by individual sensors to different extents. Accordingly, some portion of the difference between the measurements made by two sensors can be attributed to background noise. In some embodiments, non-parametric statistical methods may be used to estimate the influence of background noise levels on the difference between individual sensor measurements. Once statistics are known, a threshold value for a can be chosen at a certain confidence level. The confidence level is the probability that the true value for a lies below the threshold.

For example, measurement reports from a large number of samples of blanks (without particles) or near-blanks may be collected. The differences between sensor measurements for each sample are calculated, and a histogram plotting the frequency of occurrence of various measurement differences is generated. Histogram 631, in FIG. 6B, shows a plot of the frequency of occurrence of measurement differences in a blank sample. Histogram 632, in FIG. 6B, shows a plot of the cumulative frequency of occurrence of a measured difference as a percentage of the total frequency. In some embodiments, a threshold value for a may be chosen at the cumulative frequency below which 99% of the measured differences lie, or at any another appropriate confidence interval. As shown in FIG. 6B, in histogram 632, 99% of measured differences between the sensors are below 0.15. Therefore, the value for a may be set at 0.15 for the instrument in question according to some embodiments of the present invention.

In FIG. 6A, parameter b is designed to capture the difference in particle count between apertures due to random processes. Ideally, two sensors should produce identical particle counts. However, in practice, two sensors will generally produce different results because sample volumes and measurement times are finite. Measurement differences on account of sample volume and measurement time limitations are related to the total number of particles that have been sampled. Typically, the measurement difference is inversely proportional to the total number of particles sampled. As the total number of particles sampled increases, measurement differences between the sensors decrease. Accordingly, measurement differences may be more pronounced for samples with lower particulate concentrations. It is understood of course that other confidence levels may be selected when setting parameters. It is also understood that histograms 631 and 632 are for illustrative purposes only and that other instruments may provide different values, even at a confidence value of 0.99.

In some embodiments, the Poisson distribution may be used to model measurement differences between two sensors on account of finite sample volumes. If the expected number of particles from a collection is $\lambda$, then for a particular collection, assuming a Poisson distribution, the probability to collect exactly n number of particles is $$p(n)=(e^{-\lambda} \cdot \lambda^n)/n! \quad (1)$$

When $\lambda$ is large (more than 1000, for example), the Poisson distribution can be approximated by a normal distribution, where the probability to collect exactly n number of particles is $$p(n) = \frac{1}{\sqrt{2\pi}\,\sigma} e^{-\frac{(n-\mu)^2}{2\sigma^2}} \quad (2)$$

where $\mu=\lambda$, is the mean number of particles measured, and the standard deviation is $\sigma=\text{Sqrt}(\lambda)$.

Moreover, the difference between two independent normal distributions denoted by the suffixes 1 and 2, respectively, is also a normal distribution with a mean difference $\mu_{12}=\lambda_1-\lambda_2$ and standard deviation $\sigma_{12}=\text{Sqrt}(\lambda_1+\lambda_2)$. Thus, the probability of a difference in particle counts between sensors 1 and 2 for a given sample denoted by $p_{12}(n)$ may also be determined using equation (2) with $\lambda_1=\lambda_2=\lambda$, so that $\mu_{12}=0$ and $\sigma_{12}=\text{Sqrt}(\lambda_1+\lambda_2)=\text{Sqrt}(2\lambda)$.

In some embodiments, $\lambda$ may be replaced by the average value $V_{12}$ between the two sensors multiplied by instrument factors such as dilution ratio, flow rate, and unit conversion constants. In some embodiments, n may be replaced by the absolute value of the difference in particle counts between two sensors. If an appropriate confidence interval is chosen for $p_{12}(n)$ then b may be calculated. In some embodiments, a 99% confidence interval may be used.

In particle counters, several other factors may also contribute to a difference in measurements including, for example, physical differences between the sensors, differences in sample collection time, differences in sample volume, differences in sample dilution ratio, differences in aperture volume; differences in threshold above noise level of the pulse; and differences in physical properties of the fluid delivery system, such as the flow rate. These differences, while more pronounced in samples with high particle concentrations, generally result in a constant percentage change over the entire dynamic range. In some embodiments, a value for c may be chosen during calibration time to account for variations based on these factors.

Steps in exemplary flowchart 600, shown in FIG. 6A, may be invoked as part of histogram voting and averaging routine 530. In some embodiments, algorithm 600 may be invoked from, or as part of algorithm 500, as indicated by connector 530.

In some embodiments, in step 612 initial values for indexes i and j may be assigned. In step 614, the average count $V_{ij}$ is calculated as the average of counts $V_i$ and $V_j$ measured by sensors i and j, respectively. In step 616, the absolute value of the difference between measured counts $V_i$ and $V_j$ is compared with a+b Sqrt($V_{ij}$)+c$V_{ij}$, where a may be the background noise level parameter, b may be the random particle distribution parameter, and c may be the instrument based parameter, as described above.

Particle counts measured by sensors i and j are marked as different, in step 618, if the absolute value of the difference between measured counts $V_i$ and $V_j$ exceeds a+b Sqrt($V_{ij}$)+c$V_{ij}$. In some embodiments, the values of parameters a, b, and c may be determined during instrument calibration, or may be provided by a manufacturer. In some embodiments, the values of parameters a, b, and c may be available to software executing on particle counter/analyzer 180 or computing devices 110. On the other hand, in step 628, if the absolute value of the difference between measured counts $V_i$ and $V_j$ is less than or equal to a+b Sqrt($V_{ij}$)+c$V_{ij}$, then the particle counts measured by sensors i and j are marked as similar.

In step 620, the value of index j is checked. If the particle count by sensor 1 has not been compared with the remaining sensors (j<3), then in step 622, index j is incremented and the algorithm loops and returns to step 614 so that the particle counts of sensors 1 and 3 may be also be compared. In step 620, if j≧3, then the algorithm proceeds to step 624, where the value of index i is checked. If the particle counts by sensors 2 and 3 have not been compared (i<2) then index i is incremented and the algorithm loops and returns to step 614 so that the particle counts of sensors 2 and 3 may be also be compared. If particle counts by all sensors have been compared and marked the algorithm proceeds to step 681.

FIG. 6C shows an exemplary flowchart 650 depicting steps in an alternate method for determining when a particle count measured by a sensor is considered different from that measured by another sensor in a three-sensor particle counter. In some embodiments, the exemplary algorithm depicted by flowchart 650 may use a comparison of histograms generated from particle count measurements made by various sensors in order to determine when particle counts are in conformity, or when they are to be considered different. Steps in exemplary flowchart 650, shown in FIG. 6C, may be invoked as part of histogram voting and averaging routine 530. In some embodiments, algorithm 650 may be invoked from, or as part of algorithm 500, as indicated by connector 530.

Figure 6E:
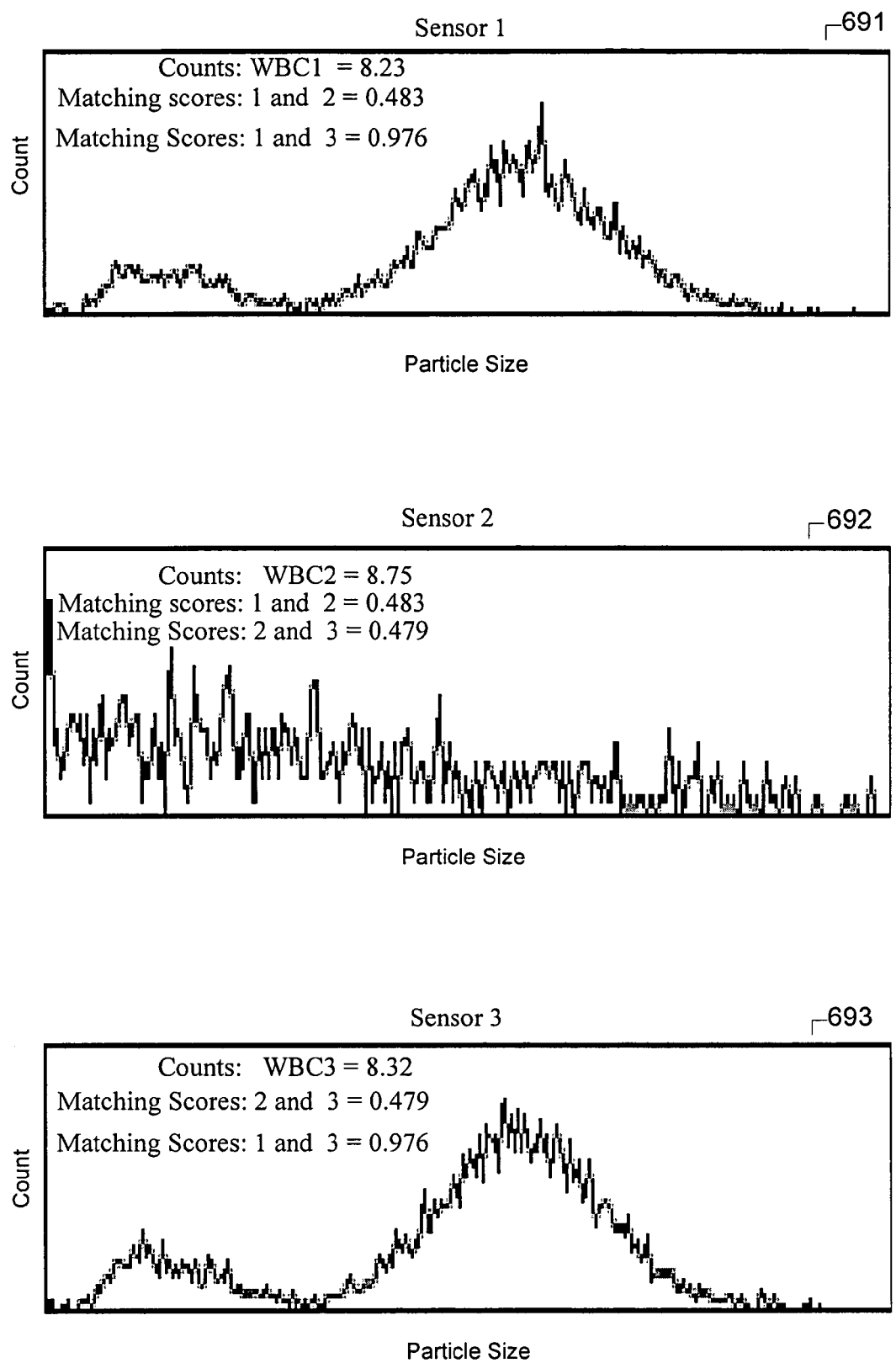
FIG. 6E shows three exemplary histograms indicating the distribution of WBC particle sizes as measured by three sensors in a particle counter.

FIG. 6E shows three exemplary histograms 691, 692, and 693 indicating the distribution of WBC particle sizes as measured by three sensors—Sensor 1, Sensor 2, and Sensor 3, respectively, in a particle counter. In some embodiments, the algorithm depicted flowchart 650 may operate on particle count data depicted by the histograms shown in FIG. 6E. As shown in FIG. 6E, the total particle counts for sensors 1, 2, and 3 are given by 8.23, 8.75, and 8.32, respectively. Accordingly, an analysis for sensor malfunction based on a simple comparison of the individual particle count totals may not detect any problems because the total particle counts as measured by the three individual sensors may not be considered as differing significantly. However, as shown in FIG. 6E, the shape of histogram 692 representing the particle size distribution as measured by sensor 2, is different from histograms 691 and 693 measured by sensors 1 and 3, respectively and may indicate a problem or a malfunction with sensor 2.

In some embodiments, the exemplary algorithm depicted by flowchart 650 may use a comparison of histograms, or a comparison of particle size distributions generated from particle count measurements made by various sensors in order to determine when particle counts are in conformity, or when they are to be considered different. It should be noted that the described methods are exemplary only and that other well-known methods are available for histogram comparison including minimum distance classifier, matching by correlation etc. The above-identified methods and others are detailed in "Digital Image Processing," pp. 580-586, Rafael C. Gonzalez and Richard E. Woods, Addison-Wesley, 1993, which is herein incorporated by reference in its entirety. For the purposes of describing steps in flowchart 650, a histogram $H_i$ corresponding to measurements made by sensor i may be seen as classifying particles into a set of N bins, where each bin represents a range of particle sizes.

In some embodiments, in step 652 initial values for indexes i and j may be assigned. In step 654, a threshold value T may set for the allowable difference between the particle count measurements by two sensors. A threshold value closer to 1, would indicate that a greater degree of similarity is desired. In some embodiments, a threshold value of around 0.9 may be used. In some embodiments, the threshold value may be chosen using empirical and/or statistical methods, or from other equipment data, including calibration charts provided by a manufacturer.

In some embodiments, a similarity score may be calculated, in step 670, in order to quantify the degree of similarity between the histograms being compared. If the similarity score is 1, then the histograms are identical. In some embodiments, the similarity score may be calculated as:

$$\text{score} = \frac{\sum_{n=0}^{N-1} H_{i,n} * H_{j,n}}{\sqrt{\sum_{n=0}^{N-1} (H_{i,n} * H_{i,n}) \sum_{n=0}^{N-1} (H_{j,n} * H_{j,n})}} \quad (3)$$

where, $H_{i,n}$ represents the particle count for the $n^{th}$ bin in histogram $H_i$ corresponding to measurements made by sensor i;

$$\sum_{n=0}^{N-1} H_{i,n} * H_{j,n}$$

represents the summation of the product of particle counts in each of the corresponding individual bins of histograms $H_i$ and $H_j$, $$\sum_{n=0}^{N-1} H_{i,n} * H_{i,n}$$

represents the summation of the squares of particle counts in each individual bin of histogram $H_i$, $$\sum_{n=0}^{N-1} H_{j,n} * H_{j,n}$$

represents the summation of the squares of particle counts in each individual bin of histogram $H_j$; and N represents the total number of bins in the various histograms. In some embodiments, other measures for establishing the degree of similarity between two histograms may be used. For example, the ratio of the average absolute difference in particle counts between corresponding bins in the two histograms, and the average particle count in corresponding bins in the two histograms may be used to determine if the histograms are similar. If the ratio is low, (for example, 0.1 or less) the histograms may be considered similar. In general, the value of the ratio used to determine the similarity of two histograms may be based on empirical data obtained from experiments, or from calibration charts, or other information provided by the manufacturer.

In step 656, a similarity score computed by equation (3) is compared with threshold value T. If the computed similarity score is less than threshold value T then histograms $H_i$ and $H_j$ from sensors i and j respectively are marked as different, in step 658; otherwise histograms $H_i$ and $H_j$ from sensors i and j respectively are marked as similar, in step 668. In step 660, the value of index j is checked. If the histogram corresponding to sensor 1 has not been compared with the histograms of the remaining sensors (j<3), then in step 662, index j is incremented and the algorithm loops and returns to step 670 so that the histograms of sensors 1 and 3 may be also be compared. In step 660, if j≧3, then the algorithm proceeds to step 664, where the value of index i is checked. If the histograms corresponding to sensors 2 and 3 have not been compared (i<2) then index i is incremented and the algorithm loops and returns to step 670 so that the histograms corresponding to sensors 2 and 3 may be also be compared. If the histograms corresponding to all sensors have been compared and marked the algorithm proceeds to step 681.

FIG. 6D shows an exemplary flowchart 680 illustrating steps in an algorithm to determine when the particle count by a sensor should be rejected. In some embodiments, a count by a sensor may be rejected if that sensor's particle count has been marked as different from the particle counts of the other two sensors. Steps in exemplary flowchart 680, shown in FIG. 6D, may be invoked as part of histogram voting and averaging routine 530. In some embodiments, algorithm 680 may be invoked from, or as part of algorithms 600 and/or 650, as indicated by connector 681.

In some embodiments of an exemplary algorithm to determine when the particle count by a sensor should be rejected, an index i may be initially set to 1 in step 682. In step 684, a count $V_i$ may be rejected if count $V_i$ has been previously marked as different from counts by all other sensors in the instrument. For example, count $V_1$ may be rejected if it has been marked as different from counts $V_2$ and $V_3$. In some embodiments, the particle counts may have been marked as different by algorithms depicted in flowcharts 600 and/or 650. In step 686, index i is checked to see if all sensors in the instrument have been processed. In a particle counter embodiment with 3 sensors, if i<3, then i may be incremented in step 688 and the algorithm loops back to step 684, where the count by the next sensor i may be processed.

In step 690, if the counts by all sensors have been marked as different from the counts by all other sensors, then in step 692, an error condition relating to an instrument malfunction may be flagged and an operator may be alerted. In some embodiments, the algorithm may flash an error message through an appropriate user interface alerting the operator about a possible instrument malfunction and the need for a re-test. In some embodiments of the present invention, in step 696, the algorithm may terminate after the error condition has been detected and flagged. In some embodiments, all sensors whose counts have been rejected may be tagged as malfunctioning and an operator may be alerted. In some embodiments, rejected sensors may be logged in a log file.

In some embodiments, in step 694, all valid (non-rejected) counts are averaged. The averaged count and statistics pertaining to the averaged count may be stored and/or reported. In some embodiments, if a sensor is voted out the measurements made by the other sensors may be averaged. In some embodiments, a new pulse-edited, normalized, and averaged histogram may be generated by averaging all valid (non-rejected) histograms. In some embodiments, histograms may be averaged by averaging particle counts for corresponding bins in the various histograms. In some embodiments, the averaged histogram may be generated from the total average particle count for each bin j, $C_j$, using equation (4) below, $$C_j = \frac{\left(\sum_{i=0}^{S-1} H_{i,j}\right)}{S}, \tag{4}$$

where, $H_{i,j}$ represents the $j^{th}$ bin of histogram $H_i$, and S is the total number of valid histograms. For example, if no measurement is rejected in a three sensor particle counter then S=3. Other statistical methods may also be used to combine the measurements in the individual histograms in a manner consistent with embodiments of the invention. In some embodiments, the algorithm may then terminate in step 540.

FIG. 6E shows three exemplary histograms 691, 692, and 693 indicating the distribution of WBC particle sizes as measured by three sensors—Sensor 1, Sensor 2, and Sensor 3, respectively, in a particle counter. As shown in FIG. 6E, the shape of histogram 692 representing the particle size distribution as measured by sensor 2, is different from histograms 591 and 593 measured by sensors 1 and 3, respectively. Note that the similarity score obtained by comparing histograms 1 and 2 is 0.483, and the similarity score obtained by comparing histograms 2 and 3 is 0.479. This compares unfavorably with the similarity score of 0.976 obtained by comparing exemplary histograms 1 and 3. If an appropriate threshold T is set, the count by sensor 2 may be rejected. In some embodiments, sensor 2 may be logged and/or tagged as a malfunctioning sensor. In some embodiments, the counts by sensors 1 and 3 may be averaged, using equation (4), above, with S=2, to obtain a new pulse-edited, averaged histogram.

FIG. 7 shows an exemplary flowchart 700 depicting steps in an algorithm for measurement and analysis of particle parameters according to some embodiments of the present invention. In some embodiments, the algorithm depicted by exemplary flowchart 700 may be executed by computing device 110 and/or particle counter/analyzer 180. In some embodiments, the algorithm commences in step 510 and enters a pulse editing routine in step 515. As described above with respect to FIG. 5, pulse editing routine 515 may identify and eliminate misshapen pulses according to some embodiments of the present invention.

In step 520, the pulse edited histogram obtained at the completion of the pulse editing routine in step 515 may be normalized according to some embodiments of the present invention. As described above with respect to FIG. 5, in some embodiments, normalization may involve the computation or re-computation of the relative frequencies of occurrence for each of the individual bins in the histogram based on the total number of pulses remaining after step 515. In some embodiments, the number of pulses remaining in each bin (following the removal of aberrant pulses) may be divided by the total number of remaining pulses to obtain the relative frequencies of occurrence for each of the individual bins.

Routines executed in steps 515 and 520 reduce inaccuracies on account of misshapen pulses. To further increase the accuracy and reliability of the particle count, the effects of particle coincidence also need to be addressed. Coincidence tends to increase at higher particle concentration levels causing inaccuracies in particle measurements and effectively limiting the range of operation of flow cytometers. On one hand, coincidence may create a larger than usual pulse, which may cause the coincident particles to be mistaken for a larger particle. As a result, the count of the larger particle is erroneously increased by one, but the counts for the individual (smaller-sized) coincident particles are not incremented leading to an incorrect lower count for each coincident particle type. This phenomenon is termed vertical interaction. Vertical interaction causes the mean particle size to be skewed toward larger particle sizes. The total cumulative particle volume, however, remains unaffected.

On the other hand, in some situations, such as when two particles pass through the sensing zone of a flow cytometry instrument in close proximity, the instrument may register only a single pulse corresponding to one of the particles. This phenomenon is termed horizontal interaction and results in a lower cumulative particle volume and in a lower particle count.

In step 720, as described above with respect to FIG. 7, a mathematical analysis of the normalized (and pulse-edited) histogram may be performed according to some embodiments of the present invention. In some embodiments, the mathematical analysis may serve to reduce the effects of particle coincidence. In some embodiments, the mathematical analysis may comprise the steps of: performing a Fourier transform of the normalized histogram; determining a probability that there is at least one particle in the sensing zone; calculating a Fourier transform of a corrected histogram based on the normalized histogram and the probability that there is at least one particle in the sensing zone; and performing an inverse Fourier transform on the calculated Fourier transform of the corrected histogram. In some embodiments, the Fourier transform and its inverse may be performed by fast Fourier methods. In some embodiments, Laplace transforms, or other mathematical transforms may be used in place of Fourier transforms. Fourier and Laplace transforms are generally known.

In some embodiments, the sensing zone of particle counter/analyzer 180 may be the volume occupied by aperture 30. In some embodiments, the sensing zone may refer to a volume that includes the volume occupied by aperture 30 within which a particle causes an appreciable change in the impedance of aperture 30. In some embodiments, the size of the sensing zone may be determined when particle counter/analyzer 180 is calibrated, or based on design parameters. In some embodiments, the sensing zone volume for a particle counter/analyzer may be further modified following a measuring cycle based on the average height of pulses generated by particle counter/analyzer 180.

If the particle count is n; the volume of the sensing zone is z; and the volume of particle suspension 80 sampled during the count is $\Delta V$; then the probability that there is at least one particle in the sensing zone x is given by, $$x = \frac{zn}{\Delta V}. \tag{5}$$

In Wynn, which has been incorporated in this application by reference in its entirety, the Fourier transform of a corrected histogram has been shown to be given by:

$$\hat{f}u(s) = \frac{\ln\left(\frac{x}{1-x}\hat{f}o(s) + 1\right)}{\ln\left(\frac{1}{1-x}\right)}, \tag{6}$$

where $\hat{f}o(s)$ is the Fourier transform of the normalized histogram and x is the probability that at any instant there is at least one particle in the sensing zone. In some embodiments, a corrected histogram may be obtained by performing an inverse Fourier transform on $\hat{f}u(s)$, the calculated Fourier transform of the corrected histogram.

In some embodiments, in step 726, a pulse width and a wait time corrected count $N_{wt}$ may be obtained from the corrected histogram. In some embodiments, the pulse width may be calculated using the mode and/or mean pulse height of pulses in the corrected histogram. In some embodiments, the pulse width is then used to determine average wait time between pulses $T_{wt}$.

At high levels of particle concentration in particle suspension 80, a particle counter/analyzer 180 may register a series of coincident particles. In some situations, the coincident particles may traverse through aperture 30 so that one particle enters aperture 30 just as another particle leaves. In such situations, the electrical pulse may resemble a series of contiguous M-shaped pulses, where the falling edge of the pulse never falls below threshold 330. Particle counter/analyzer 180 may register the contiguous M-shaped pulse as a single pulse and only increment the particle count by one, leading to an undercount of the particles.

In some embodiments, the average wait time between pulses $T_{wt}$ may be used to obtain a wait time corrected count. In some embodiments, the wait time corrected count $N_{wt}$ may correct the lowered particle count on account of misshapen pulses, including contiguous M-shaped pulses, in step 515. In some embodiments, the wait time corrected count $N_{wt}$ may be calculated as:

$$N_{wt} = \frac{N_0}{T_{wt} + (N_0 * f_{FT})}, \quad (7)$$

where, $f_{FT}$ represents a flight time correction factor. The flight time correction factor is indicative of the time taken by a particle to traverse the sensing zone and may be calculated as a function of the mode and/or mean pulse height of pulses in the corrected histogram.

The $f_{FT}$ for an aperture may also be estimated from the particle size information on the histogram. In one embodiment, pulse widths may be directly estimated from stored measurements. Pulse widths may also be estimated by using empirical studies and/or statistical methods to establish a relationship between pulse heights and pulse widths. In some embodiments, $f_{FT}$ may be obtained as a function of pulse widths, where the pulse widths may be calculated based on a mean pulse height and mode pulse height of the coincidence corrected histogram. In some embodiments, pulse widths may be calculated based, on some function of the mean particle size and mode particle size in the coincidence corrected histogram. Note that because pulse heights are proportional to particle sizes the calculation of pulse widths may be also based on some function of the mean pulse height and mode pulse height in the coincidence corrected histogram. In general, the interrelationships between particle size, pulse width, pulse height, and other pulse or signal parameters may be exploited to calculate flight time correction factor $f_{FT}$.

In step 730, exemplary algorithm 700 may calculate the coincidence corrected count N, which is given by:

$$N = \frac{1}{z} \ln\left(\frac{1}{1 - (z * N_{wt})}\right), \quad (8)$$

where, z the volume of the sensing zone. In some embodiments, equations (7) and (8) above operate in conjunction to correct the raw count of particle counter/analyzer 180, without causing a corresponding increase in the total particle volume. Additionally, as noted above, accuracy is further increased by obtaining and using a wait time corrected count to derive the corrected count of equation (8). The wait time corrected count helps to account for missed particle counts due to misshapen pulses. In some embodiments, total volume may be increased proportionately when the missed particles are added back to the total count, thus leading to a more accurate estimation of total particle volume. In some embodiments, accuracy is further enhanced by the use of a plurality of parameters to identify misshapen pulses during a pulse editing step, and eliminate these pulses from further consideration.

FIG. 8 shows an exemplary flowchart 800, depicting steps in an algorithm for measurement and analysis of particle parameters according to some embodiments of the present invention. In some embodiments, each step in algorithm may correspond to a pre-defined routine. In some embodiments, one or more of the steps in flowchart 800 may be executed by one or more of algorithms depicted in FIGS. 5, 6A, 6C, 6D, and 7. In some embodiments, algorithm 800 may be executed by computing device 110 and/or particle counter/analyzer 180.

In some embodiments, the algorithm commences in step 510 and enters a pulse editing routine in step 515. As described with respect to FIG. 5 above, pulse editing routine 515 may identify and eliminate misshapen pulses according to some embodiments of the present invention. In some embodiments, pulse editing may be performed for pulses generated by each sensor in a multi-sensor particle counter/analyzer 180.

In step 520, the pulse edited histogram obtained at the completion of the pulse editing routine in step 515 may be normalized according to some embodiments of the present invention. As described with respect to FIG. 5 above, in some embodiments, normalization may involve the computation or re-computation of the relative frequencies of occurrence for each of the individual bins in the histogram based on the total number of pulses remaining after step 515. In some embodiments, the number of pulses remaining in each bin (following the removal of aberrant pulses) may be divided by the total number of remaining pulses to obtain the relative frequencies of occurrence for each of the individual bins. In some embodiments, normalization may be performed for histograms corresponding to particle counts generated by each sensor in a multi-sensor particle counter/analyzer 180.

In histogram voting and averaging routine 530, as described with respect to FIGS. 5, 6A, 6C, and 6D above, a histogram that is determined to be different from all other histograms generated by particle counter/analyzer 180 may be voted out. In some embodiments, algorithms such as exemplary algorithms illustrated in FIGS. 6A, 6C, and 6D may be used to determine if a histogram corresponding to measurements made by a sensor should be voted out. In some embodiments, the algorithms depicted in the exemplary flowcharts shown in FIGS. 6A, 6C, and 6D may be used to perform some or all of histogram voting and averaging routine 530. In some embodiments, measurements by non-rejected sensors in a multi-sensor particle counter/analyzer may be averaged or statistically combined in a manner consistent with embodiments of the present invention.

In step 720, as described with respect to FIG. 7 above, a mathematical analysis of the normalized, pulse-edited, and averaged histogram may be performed according to some embodiments of the present invention. In some embodiments, the mathematical analysis may the comprise steps of: performing a Fourier transform of the normalized histogram; determining a probability that there is at least one particle in the sensing zone; calculating a Fourier transform of a corrected histogram based on the normalized histogram and the probability that there is at least one particle in the sensing zone; and performing an inverse Fourier transform on the calculated Fourier transform of the corrected histogram. In some embodiments, the Fourier transform and its inverse may be performed by fast Fourier methods. In some embodiments, Laplace transforms, or other mathematical transforms may be used in place Fourier transforms.

In some embodiments, in step 726, a pulse width and a wait time corrected count $N_{wt}$ may be obtained from pulse height data in the corrected histogram as described with respect to FIG. 7 above. In some embodiments, the pulse width may be calculated using the mode and/or mean pulse height of pulses in the corrected histogram. The wait time is a measured property of the system and is used along with pulse width to calculate wait time corrected count. In some embodiments, the pulse width is then used to determine average wait time between pulses $T_{wt}$. In step 730, exemplary algorithm 800 may calculate the coincidence corrected count N, as given by equation (8) above, before terminating in step 840.

Further, methods consistent with embodiments of the invention may conveniently be implemented using program modules, hardware modules, or a combination of program and hardware modules. Such modules, when executed, may perform the steps and features disclosed herein, including those disclosed with reference to the exemplary flow charts shown in the figures. The operations, stages, and procedures described above and illustrated in the accompanying drawings are sufficiently disclosed to permit the practice of the invention. Moreover, there are many computers and operating systems that may be used in practicing embodiments of the instant invention and, therefore, no detailed computer program could be provided that would be applicable to these many different systems. Each user of a particular computer will be aware of the language, hardware, and tools that are most useful for that user's needs and purposes.

The above-noted features and aspects of the present invention may be implemented in various environments. Such environments and related applications may be specially constructed for performing the various processes and operations of the invention, or they may include a general-purpose computer or computing platform selectively activated or reconfigured by program code to provide the functionality. The processes disclosed herein are not inherently related to any particular computer or other apparatus, and aspects of these processes may be implemented by any suitable combination of hardware, software, and/or firmware. For example, various general-purpose machines may be used with programs written in accordance with teachings of the invention, or it may be more convenient to construct a specialized apparatus or system to perform the required methods and techniques.

Embodiments of the present invention also relate to computer readable media that include program instructions or program code for performing various computer-implemented operations based on the methods and processes of embodiments of the invention. The program instructions may be those specially designed and constructed for the purposes of the invention, or they may be of the kind well known and available to those having skill in the computer software arts. Examples of program instructions include, for example, machine code, such as produced by a compiler, and files containing a high-level code that can be executed by the computer using an interpreter.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for particle counting based on electrical signals output from sensors in a flow cytometer instrument, comprising the following steps implemented with a processor:
    generating a normalized histogram based on captured electrical signals associated with a first sensor in the flow cytometer instrument;
    obtaining a corrected histogram based on a mathematical analysis of the normalized histogram and a probability that at any instant there is at least one particle in a sensing zone of the flow cytometer instrument;
    performing a determination based on the corrected histogram and one or more histograms associated with respective one or more second sensors to obtain particle counts;
    outputting the particle counts;
    comparing parameters of each captured electrical signal with corresponding reference parameter ranges; and
    choosing captured electrical signals whose parameters fall within corresponding reference parameter ranges;
    wherein generating the normalized histogram is based on the chosen captured electrical signals.

2. The method of claim 1, wherein parameters of the captured electrical signals include one or more of signal amplitude, Peak, H50, T50, T75, and the ratios T75/T50 and Peak/H50.

3. A method for particle counting based on electrical signals output from sensors in a flow cytometer instrument, comprising the following steps implemented with a processor:
    generating a normalized histogram based on captured electrical signals associated with a first sensor in the flow cytometer instrument;
    obtaining a corrected histogram based on a mathematical analysis of the normalized histogram and a probability that at any instant there is at least one particle in a sensing zone of the flow cytometer instrument;
    performing a determination based on the corrected histogram and one or more histograms associated with respective one or more second sensors to obtain particle counts, wherein performing the determination includes (i) calculating a first particle count based on the corrected histogram and (ii) comparing the first particle count and one or more second particle counts based on the one or more histograms associated with the respective one or more second sensors to determine whether the first particle count is to be rejected from an averaged particle count calculation; and
    outputting the particle counts,
    wherein the wait-time corrected count and the coincidence corrected count are calculated based on a function of one or more of a mode signal height parameter and a mean signal height parameter of the corrected histogram.

4. A system comprising:
    a particle counter coupled to a processor and memory, wherein the particle counter captures electrical signals generated when a particle traverses a sensing zone and the memory contains instructions for controlling a processor to
    generate a normalized histogram based on captured electrical signals associated with a first sensor in a flow cytometer instrument;
    obtain a corrected histogram based on a mathematical analysis of the normalized histogram and a probability that at any instant there is at least one particle in the sensing zone; and
    perform a determination based on the corrected histogram and one or more histograms associated with respective one or more second sensors, wherein the memory contains the instructions for controlling the processor to
    compare parameters of each captured electrical signal with corresponding reference parameter ranges; and
    choose captured electrical signals whose parameters fall within corresponding reference parameter ranges;
    wherein the normalized histogram is based on the chosen captured electrical signals.

5. The system of claim 4, wherein parameters of the captured electrical signals include one or more of signal amplitude, Peak, H50, T50, T75, and the ratios T75/ T50 and Peak/H50.

6. A system for measuring particulate counts suspended in solutions wherein the system comprises:
    means for generating a normalized histogram by selecting captured electrical signals wherein a captured electrical signal is associated with one or more sensors in a flow cytometer instrument;

means for obtaining a corrected histogram based on a mathematical analysis of the normalized histogram and a probability that at any instant there is at least one particle in a sensing zone of the flow cytometer instrument; and means for calculating corrected particle counts based on the corrected histogram;

wherein the means for generating the normalized histogram includes means for comparing parameters of each captured electrical signal with corresponding reference parameter ranges, means for choosing captured electrical signals whose parameters fall within corresponding reference parameter ranges, means for generating at least one edited histogram for each sensor using the chosen electrical signals associated with the sensor, means for rejecting an edited histogram associated with a sensor, if the edited histogram differs from all distinct edited histograms associated with other sensors, means for averaging all non-rejected edited histograms, and means for normalizing the averaged histogram.

7. The system of claim 6, wherein the means for rejecting the edited histogram includes means for determining a statistical threshold value for deciding histogram similarity;

means for computing similarity scores for the edited histogram associated with the sensor by comparing the edited histogram associated with the sensor with every distinct histogram; and means for rejecting the edited histogram associated with the sensor, if every similarity score computed for the edited histogram associated with the sensor is less than the statistical threshold value.

8. An article comprising a computer-readable medium that stores instructions which when executed by a processor enable the processor to:

generate a normalized histogram based on captured electrical signals associated with a first sensor of a plurality of sensors in a flow cytometer instrument;

obtain a corrected histogram based on a mathematical analysis of the normalized histogram and a probability that at any instant there is at least one particle in the sensing zone; and perform a determination based on the corrected histogram and one or more histograms associated with respective one or more second sensors of the plurality of sensors;

compare parameters of each captured electrical signal with corresponding reference parameter ranges; and choose captured electrical signals whose parameters fall within corresponding reference parameter ranges;

wherein the normalized histogram is generated based on the chosen captured electrical signals.

* * * * *